United States Patent [19]

Corson et al.

[11] B 3,996,249

[45] Dec. 7, 1976

[54] ISOMERIZATION PROCESS

[75] Inventors: Ben B. Corson, Milwaukee, Wis.; William T. Gormley, Pittsburgh, Pa.

[73] Assignee: Koppers Company, Inc., Pittsburgh, Pa.

[22] Filed: Aug. 29, 1973

[21] Appl. No.: 392,798

[44] Published under the second Trial Voluntary Protest Program on March 30, 1976 as document No. B 392,798.

Related U.S. Application Data

[63] Continuation-in-part of Ser. No. 123,075, March 10, 1971, abandoned.

[52] U.S. Cl. .................... 260/346.3; 260/2 EA
[51] Int. Cl.² ............................... C07D 307/89
[58] Field of Search ............. 260/346.3, 468 L

[56] References Cited

UNITED STATES PATENTS

| | | | |
|---|---|---|---|
| 2,764,597 | 9/1956 | Barney | 260/346.3 |
| 3,169,975 | 2/1965 | Schulz | 260/346.3 |
| 3,341,555 | 9/1967 | Wooster et al. | 260/346.3 |
| 3,487,092 | 12/1969 | Cheng et al. | 260/346.3 |
| 3,647,701 | 3/1972 | Robinson et al. | 252/182 |

OTHER PUBLICATIONS

Shriner et al., The Systematic Identification of Organic Compounds, Fifth Edition, New York, John Wiley, 28–29.

*Primary Examiner*—Henry R. Jiles
*Assistant Examiner*—Bernard I. Dentz
*Attorney, Agent, or Firm*—Oscar B. Brumback; Herbert J. Zeh, Jr.

[57] ABSTRACT

The delta-4 isomer of tetrahydrophthalic anhydride is isomerized in the presence of a catalytic amount of palladium and selected acid anhydrides that liquify the normally solid delta-4 isomer at a temperature below its melting point. This permits the isomerization to be effected at relatively low temperatures and in relatively short times to produce a mixture of isomers of tetrahydrophthalic anhydride that is in the liquid state at temperatures in the range of room temperature.

11 Claims, No Drawings

ISOMERIZATION PROCESS

CROSS-REFERENCE TO RELATED APPLICATION

This is a continuation-in-part of our co-pending application Ser. No. 123,075, filed Mar. 10, 1971 and now abandoned.

FIELD OF THE INVENTION

This invention relates to the catalytic isomerization of tetrahydrophthalic anhydride at relatively low temperatures. More particularly, this invention relates to the low-temperature production of a mixture of isomers of tetrahydrophthalic anhydride which mixture is in the liquid state at room temperature.

Tetrahydrophthalic anhydride has 4 isomers with respect to the position of the double bond. They are:

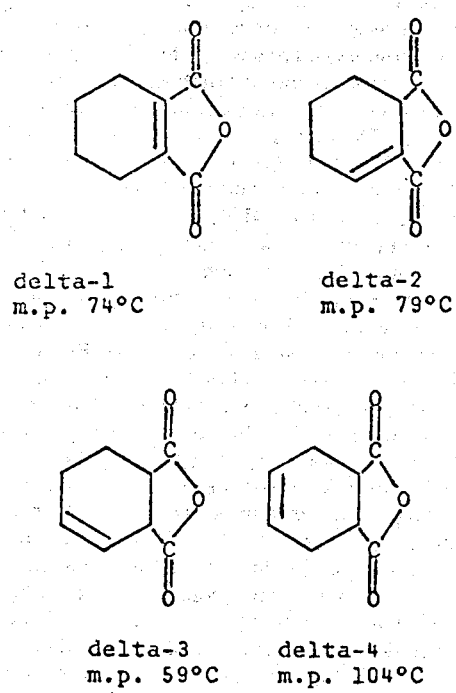

delta-1 m.p. 74° C delta-2 m.p. 79° C delta-3 m.p. 59° C delta-4 m.p. 104° C

The most readily available isomer is delta-4 tetrahydrophthalic anhydride, referred to also as 4-cyclohexene-1,2-dicarboxylic anhydride. The delta-4 isomer, which is available commercially, is made economically by reacting maleic anhydride and 1,3-butadiene. This reaction, which can produce the delta-4 isomer in substantially quantitative yields, does not produce the delta-1, delta-2 or delta-3 isomers of tetrahydrophthalic anhydride.

It has been recognized that mixtures of the aforementioned isomers which mixtures are liquid at room temperature can be used to better advantage in some applications than the solid delta-4 isomer. (From the melting point data reported below the structural formulas set forth hereinabove, it can be seen that each of the isomers is a solid at room temperature. However, there can be prepared isomeric mixtures which have melting points lower than the lowest melting point isomer present in the mixture; and isomeric mixtures which are in the liquid state at room temperature are known.) For example, the use of a liquid mixture of tetrahydrophthalic anhydride isomers as an epoxy resin hardner or curing agent has advantages over the use of a solid anhydride. Also, for isomeric mixtures which are solids at room temperature, the general rule is that the lower their freezing points, the more advantageous their use as epoxy resin hardeners. This is because the pot life of the epoxy resin/anhydride mixture is longer, the lower the freezing point of the anhydride; and best results are obtained when the anhydride is in the liquid state at room temperature. The longer pot life provides very important material handling advantages.

This invention relates to the production of an isomeric mixture of tetrahydrophthalic anhydride which is in the liquid state at temperatures in the range of room temperature or which has a melting or freezing point below that of the isomer in the mixture with the lowest freezing or melting point.

REPORTED DEVELOPMENTS

Heretofore known methods for the catalytic production of mixtures of isomers of tetrahydrophthalic anhydride are carried out at relatively high temperatures or they have other disadvantages.

U.S. Pat. No. 2,764,597 discloses the isomerization of delta-4 tetrahydrophthalic anhydride in the presence of a palladium or ruthenium catalyst to isomeric mixtures containing 40% to 75% of the delta-1 isomer. The recommended temperature of reaction is between 150° and 220° C.

In U.S. Pat. No. 2,959,599, there is disclosed the isomerization of delta-4 tetrahydrophthalic anhydride to isomeric liquid mixtures by utilizing an acid catalyst at temperatures desirably of about 150° C and above. This method tends to produce acidic coke by-products which have to be filtered from the anhydrides and which are difficult to remove from the reactor. Furthermore, the reaction product must be distilled to separate the anhydrides from acid contaminants.

Another catalytic method for isomerizing solid tetrahydrophthalic anhydride to a liquid mixture of isomers is disclosed in U.S. Pat. No. 3,470,214. The catalyst is a silica-alumina cracking catalyst having a quinoline number of at least 0.01. The temperature at which the reaction should be maintained is given as 100° C to 250° C, though it is noted that "of course" the temperature must be above the melting point of the starting material. The temperatures used in the examples of the patent are well in excess of 100° C — 180° C, 220° C to 230° C, and 230° C.

In view of the shortcomings of heretofore known methods for producing isomeric mixtures of tetrahydrophthalic anhydride, it is an object of this invention to provide an improved catalytic method for producing them.

BRIEF DESCRIPTION OF THE INVENTION

In accordance with this invention, it has been found that isomeric mixtures of tetrahydrophthalic anhydride can be prepared in the presence of (A) a catalytic amount of palladium and (B) an acid anhydride other than delta-4 tetrahydrophthalic anhydride which has a molecular weight in excess of 100 and which is a curing agent for epoxy resins. It should be understood that when the term "acid anhydride" or the phrase "acid anhydride which is a curing agent for epoxy resins" is used herein, they are not meant to include delta-4 tetrahydrophthalic anhydride, which as noted above is itself a curing agent for epoxy resins.

The presence of the acid anhydride in the palladium-catalyzed isomerization reaction mixture results in the production of liquid mixtures of isomers of tetrahydrophthalic anhydride at temperatures lower than and times quicker than those reported for heretofore known methods. Liquid isomeric mixtures of tetrahydrophthalic anhydride have been prepared within 2 hours at a temperature of 80°C in accordance with this invention.

Speaking generally, the isomerization reaction of this invention can be carried out at temperatures well below the melting point of the delta-4 tetrahydrophthalic anhydride, for instance, as low as about 60°C. Preferably, the isomerization reaction is carried out at temperatures of at least about 75°C but below the melting point of the starting material.

The present invention can be used to isomerize also derivatives of delta-4 tetrahydrophthalic anhydride, including, for example, esters thereof and lower alkyl derivatives.

As will be explained more fully below, the acid anhydride in the reaction mixture forms with the delta-4 isomer of tetrahydrophthalic anhydride a liquid mixture below the melting point of the delta-4 isomer. It is believed that this contributes to the relatively rapid, low temperature isomerization reaction. The amount of acid anhydride used in the reaction mixture can vary over a broad range. Exemplary amounts of the acid anhydride are about 0.1 wt. % to about 20 wt. %.

The amount of palladium catalyst used in the isomerization reaction can vary over a wide range also. For example, palladium can comprise about 0.001% to about 10% by weight of the material to be isomerized.

As noted hereinabove, U.S. Pat. No. 2,764,597 discloses the use of a palladium or a ruthenium catalyst for producing an isomeric mixture of tetrahydrophthalic anhydrides containing a predominant amount of the delta-4 isomer. However, efforts to produce liquid mixtures of isomers of tetrahydrophthalic anhydride in a "low temperature, short time" isomerization reaction, by the use of ruthenium and the acid anhydride of this invention have been unsuccessful; the use of metals, such as copper, platinum, nickel and cobalt, which are closely related to palladium and which are mentioned in the aforementioned patent has met with unsuccess also.

The method of the present invention provides a number of advantages over heretofore available methods. One of the most important advantages is that isomeric mixtures in the liquid state can be produced very rapidly at moderate temperatures, for example, within 2 hours at 80°C. Another advantage is that extremely small amounts of the palladium catalyst can be utilized—for example, about 1 part of palladium to 100,000 parts of material to be isomerized. In addition, palladium has a low rate of attrition and a relatively long activity period. The palladium catalyst can be regenerated and reused for extended periods of time. Furthermore, substanitally 100% yields of isomerized product can be obtained.

The above advantages are not off-set to any significant extent by disadvantages. Very small amounts of the acid anhydride can be used to obtain the efficiencies that are realized by operating at low temperatures and shorter periods of time. In addition, the acid anhydride need not be separated from the reaction mixture when it is used as an epoxy curing agent. This is because each of the anhydrides is itself an epoxy curing agent.

DETAILED DESCRIPTION OF THE INVENTION

It is believed that the present invention will have its widest use in applications in which tetrahydrophthalic anhydride is the starting material to be isomerized. As mentioned above, the delta-4 isomer is readily available as a result of its being able to be produced economically by reacting 1,3-butadiene and maleic anhydride. However, derivatives of the delta-4 isomer can be isomerized also in the presence of palladium and acid anhydride of this invention. For example, lower alkyl (1 to about 6 carbon atoms) and polyalkyl substituted tetrahydrophthalic anhydrides can be isomerized according to this invention. Such derivatives of tetrahydrophthalic anhydride can be prepared by reacting maleic anhydride with isoprene, piperylene or hexadiene. In addition, the palladium and acid anhydride combination can be used effectively to change the proportion of isomers present in a mixture made up of different isomers of tetrahydrophthalic anhydride. Still another example of starting material that can be used is an ester of the delta-4 isomer, including mono- and dialkyl esters. The alkyl groups of such esters can have 1 to about 10 carbon atoms; examples of such groups include methyl, propyl, butyl and octyl groups.

The acid anhydrides which are used in combination with the palladium catalyst are those acid anhydrides which have molecular weights in excess of 100 and which are curing agents for epoxy resins. Such acid anhydrides are a well-recognized class of compounds. (For example, see *Handbook of Epoxy Resins* by Lee and Neville, McGraw-Hill Book Company, Inc. (1967). Additionally, to be effective the acid anhydride should have a melting point below about 140°C; and in the liquid state, it should be miscible with liquid delta-4 tetrahydrophthalic anhydride. Examples of acid anhydrides that can be used in accordance with this invention are: succinic anhydride; dodecenyl succinic anhydride; methyl succinic anhydride; cyclopentadiene adduct of maleic anhydride; methyl cyclopentadiene adduct of maleic anhydride; endic anhydride (endomethylene tetrahydrophthalic anhydride); delta-1 tetrahydrophthalic anhydride; itaconic anhydride; citraconic anhydride; 4-methyl tetrahydrophthalic anhydride; phthalic anhydride; hexahydrophthalic anhydride; and an isomeric mixture containing two or more of the delta-1, delta-2 and delta-3 isomers of tetrahydrophthalic anhydride. As will be seen from examples reported below the isomeric mixture can contain also the delta-4 isomer. Excellent results have been obtained with these materials. It should be understood that the aforementioned list is exemplary and that other acid anhydrides which have molecular weights in excess of 100 and which are curing agents for epoxy resins can be used provided that their melting point is below about 140°C and that they are miscible with the liquid delta-4 isomer.

As mentioned briefly hereinabove, the amount of acid anhydride used in the reaction mixture can vary over a wide range. It is noted that because the acid anhydrides are themselves curing agents for epoxy resins it is unnecessary to separate them from the reaction product when it is used as a curing agent for epoxy resins. From the standpoint of being effective, there appears to be no upper limit on the amount of anhydride that can be used, but certain considerations will dictate an upper limit which can be selected best by the individual user. For example, when the product of the isomerization reaction is to be used as an epoxy curing agent, the upper limit of the acid anhydride can be selected on the basis of how much of the anhydride the user wishes to have present in the curing agent mixture. If it is desired to have a large proportion of the acid anhydride present, then relatively large amounts can be used in the isomerization reaction. On the other hand, if it is desired to use a curing agent that consists principally or entirely of tetrahydrophthalic anhydrides, then very small amounts of the acid anhydride can be used.

To give some guidelines on the amount of acid anhydride that can be added to the reaction mixture, it is suggested that an amount within the range of about 0.1% to about 20% by weight be used. (The percentage is based on the weight of the acid anhydride and the material to be isomerized.) Utilizing amounts of acid anhydride within this range, liquid mixtures of tetrahydrophthalic anhydride isomers have been produced at relatively low temperatures and short reaction times. However, it should be understood that amounts outside this range can be used.

The weight proportion of palladium catalyst to material to be isomerized can vary over a wide range, for example about 1:100,000 to about 1:10 (about 0.001% to about 10%). At ratios of greater than 1:10, disproportionation may be encountered; and below 1:100,000, the amount of catalyst may be so small as to be ineffective.

The palladium catalyst may be supported or unsupported; preferably it is supported. Examples of supporting materials are alumina ($Al_2O_3$), carbon, silica gel and kieselguhr. Palladium supported on alumina or carbon (Pd-C) is available commercially and this makes it advantageous to use these support materials.

The weight proportion of catalyst to support material is not critical and may vary over a wide range. There can be used commercially available catalytic support materials which contain about 0.1% to about 20% by weight of palladium. It should be understood that the support material can comprise higher or lower proportions of the catalyst.

The isomerization can be carried out at a temperature as low as about 60°C; below this temperature, the reaction proceeds very slowly. Preferably, the reaction temperature should be at least about 75°C. At temperatures in this range and above, liquid mixtures of isomers of tetrahydrophthalic anhydride can be produced within a few hours. The upper limit on the reaction temperature is governed by the temperature at which disproportionation occurs and unwanted by-products are formed. In general, this can occur at a temperature of about 250°C and higher. In view of the excellent results that are attained at much lower temperatures, they are recommended. However, it should be understood that higher temperatures can be used. At a temperature within the range of about 75°C to 120°C, mixtures of isomers of tetrahydrophthalic anhydride which are in the liquid state at room temperature can be produced in relatively short times; this is a recommended temperature range.

A preferred sequence of steps for isomerizing delta-4 tetrahydrophthalic anhydride is to stir the palladium catalyst on its support material with the solid delta-4 isomer and thereafter add the acid anhydride to the reaction mixture as stirring is continued. The acid anhydride may be a liquid or a solid depending on the specific one used.

It has been observed that as the reaction mixture is heated, it begins to liquify, initially in the areas where the acid anhydride is present. This liquification occurs at temperatures below the melting point of the delta-4 isomer (104°C). Furthermore, when the acid anhydride is one which melts in excess of 100°C (for example, phthalic anhydride), the liquification occurs at temperatures below the melting point of both the delta-4 isomer and the acid anhydride. As heating of the reaction mixture is continued, the whole of the mixture liquifies—even at temperatures below the melting points of both the delta-4 isomer and the acid anhydride. After the isomerization has proceded to the desired extent, the catalyst can be separated from the reaction product which can then be used as is or if desired, the acid anhydride can be separated from the isomers of tetrahydrophthalic anhydride that are produced by the isomerization.

It is pointed out that the acid anhydride is a material which causes the solid delta-4 tetrahydrophthalic to liquify below its melting point, and in the case of the use of an acid anhydride which is a liquid, and a solvent for the delta-4 isomer, this can be accomplished with an amount thereof that is below that required to dissolve all of the delta-4 tetrahydrophthalic anhydride. Thus, the invention provides a method for isomerizing the delta-4 isomer of tetrahydrophthalic anhydride comprising adding to said isomer a liquid or solid material which forms a liquid mixture with said isomer at a temperature above room temperature, but below the melting point of said isomer, heating said isomer and said material to form said liquid mixture and isomerizing the liquid delta-4 isomer of said heated liquid mixture in the presence of a catalytic amount of palladium.

An integrated process can be effected in accordance with the present invention. In such a process, the reactants used to form the isomerizable material can be brought together in the presence of the palladium catalyst and acid anhydride or the palladium/anhydride combination can be added after the isomerizable material has been formed. A preferred mode of operating an integrated process for preparing and isomerizing the delta-4 isomer is as follows. Into a reactor containing a stirred mixture of palladium, acid anhydride and molten maleic anhydride, there is passed gaseous 1,3-butadiene in excess of the stoichometric amount required to react with the maleic anhydride. The reaction temperature can be maintained between about 100°C and about 250°C. The passage of the butadiene can be terminated when the butadiene take-up stops. The presence of the palladium/acid anhydride does not interfere with the formation of delta-4 tetrahydrophthalic anhydride, but the presence of the butadiene and, to a lesser extent, maleic anhydride deactivates the palladium catalyst. Nitrogen or another suitable inert gas can be used to purge the reactor of the butadiene after passage thereof has been terminated. If the catalyst has been deactivated significantly, it can be treated with a small amount of hydrogen to convert the butadiene to innocuous butane. Isomerization of the delta-4 isomer can then be effected.

Alternatively, the palladium and acid anhydride may be added to the reactor after the reactants have formed the delta-4 isomer. Or the delta-4 isomer may be transferred to a reactor containing the palladium and acid anhydride after which the mixture is heated and stirred to produce the desired product.

It is difficult and impractical to state the reaction conditions which will be effective in producing a particular type of reaction product—for example, one having predetermined amounts of the various isomers that can be produced. The difficulty arises because there are inherent in the isomerization reaction numerous variables, such as the starting material, the proportion of catalyst to material to be isomerized, the amount of acid anhydride, the reaction temperature, the time of reaction, etc. A change in any one of the variables can change the proportions of isomers which comprise the reaction product. It is suggested that a small sample of the starting material be isomerized under a set of reaction conditions and that the product be examined to determine whether it meets the desired requirements. The numerous examples reported below can be used as guidelines for selecting suitable reaction conditions.

Isomeric mixtures produced by utilizing the palladium/acid anhydride catalyst mixture of this invention can be hydrogenated easily and readily by leaving the palladium isomerization catalyst in the isomeric mixture where it will function to catalyze the hydrogenation as hydrogen is passed through the mixture. The hydrogenation will convert tetrahydrophthalic anhydride isomers to hexahydrophthalic anhydride. By partially hydrogenating the isomeric mixture, an epoxy curing agent containing both hexahydro- and tetrahydro- phthalic anhydrides can be produced and each of the anhydrides will impart its peculiar properties to the cured epoxy product. Another advantage of partially hydrogenating the isomeric mixture is that the introduction into the mixture of hexahydrophthalic anhydride with its relatively low freezing point (35°C – 37°C) will produce a product that has a lower freezing point than the starting isomeric mixture.

EXAMPLES

Examples set forth below are illustrative of the present invention. Unless otherwise stated, the apparatus used in the reactions described in the examples consisted of a 300 ml., 3-necked round bottom flask equipped with a stirrer, thermometer, reflux condenser, and gas inlet and outlet connections for nitrogen. (As a safety measure, the reaction can be carried out under a blanket of $N_2$ due to the pyrophoric nature of the catalyst.) The flask was heated with a water bath. The yields of isomers were substantially 100%. The abbreviation "THPAA" used extensively hereafter means tetrahydrophthalic anhydride. Unless stated otherwise, the symbol "%" means per cent by weight based on the total weight of the composition.

Examples 1–10 below illustrate the isomerization of delta-4 tetrahydrophthalic anhydride in the presence of palladium and different acid anhydrides according to the present invention.

Examples 1–10

In Examples 1–10, 80 grams of delta-4 tetrahydrophthalic anhydride and the acid anhydride indicated in Table 1 below in the amount indicated therein were added to a reaction flask. The % of acid anhydride was based on the amount of the anhydride and the amount of delta-4 isomer. The catalyst used was 1.5 g. of 10% Pd-90% carbon. Each of the reactions was carried out at a temperature of 80°C for the time indicated in Table 1. A slow stream of nitrogen was passed through the reaction apparatus and the subsequent suction filtration of the reaction product which was effected through a sintered glass disc. Analysis of the product was by infrared. The analysis is reported in Table 1.

TABLE 1

| Ex. No. | Additive | % of Additive | Time of Rxn., hrs. | Rxn. Product Isomeric Mixture, % ** | | | | Physical state after 2 mos. at 25°C |
|---|---|---|---|---|---|---|---|---|
| | | | | delta-1 | delta-2 | delta-3 | delta-4 | |
| 1 | hexahydrophthalic anhydride | 20 | 3 | 26 | 0 | 36 | 18 | Pale amber liquid |
| 2 | hexahydrophthalic anhydride | 11 | 4 | 25 | 0 | 47 | 17 | " |
| 3 | hexahydrophthalic anhydride | 5 | 2 | 22 | 0 | 54 | 19 | " |
| 4 | hexahydrophthalic anhydride | 5 | 5 | 28 | 0 | 52 | 15 | " |
| 5 | hexahydrophthalic anhydride | 0.4 | 2 | 31 | 0 | 55 | 14 | " |
| 6 | isomeric mixture of THPAA* | 20 | 5 | 22 | 6 | 46 | 26 | Clear, pale yellow liquid |
| 7 | isomeric mixture of THPAA* | 11 | 5 | 16 | 0 | 51 | 33 | " |
| 8 | isomeric mixture of THPAA* | 1.2 | 2 | 30 | 0 | 49 | 21 | " |
| 9 | phthalic anhydride | 20 | 5 | 26 | 0 | 41 | 13 | Thick pale amber slush |
| 10 | phthalic anhydride | 11 | 5 | 9 | 6 | 45 | 29 | Thin pale amber slush |

*12% delta-4, 72% delta-3 and 15% delta-2
** For those examples in which the % totals less than 100, the remaining portion of the reaction mixture consisted of the additive It has been found advantageous to fortify the isomeric mixture with delta-4 isomer prior to hydrogenation. The fortification makes it possible to increase considerably the delta-4 isomer throughput. The extent to which the mixture is hydrogenated can be varied as desired. It is believed that a mixture which contains hexahydrophthalic anhydride along with one or more isomers of tetrahydrophthalic anhydride will have its widest use as a curing agent for epoxy resins.

Example 11

A stirred mixture of 80 g. of delta-4 THPAA, 0.32 g. of hexahydrophthalic anhydride, and 1.5 g. of 10% Pd-90% C catalyst was heated at 80°C. for 2 hr. under a protective atmosphere of nitrogen. The reaction mixture was filtered and 77 g. of pale yellow filtrate was recovered. It analyzed as follows: 19% delta-4 THPAA; 51% of the delta-3 isomer; and 30% of the delta-1 isomer. After storage for 1.6 months at room temperature, it was still a clear yellow liquid.

Example 12

The same procedure was followed in Example 11 except that the additive was 4.2 g. of the isomeric mixture produced by the reaction of Example 11. Eighty-one grams of a pale yellow liquid containing 20% of delta-4 THPAA; 52% of the delta-3 isomer; and 28% of the delta-1 isomer were recovered.

Example 13

A stirred mixture of 20 g. of phthalic anhydride and 80 g. of delta-4 tetrahydrophthalic anhydride was melted by heating to 110°C. The resulting mixture was cooled to 80°C and 1.5 grams of 10% Pd-90% C catalyst was added to the mixture which had the appearance and consistency of a thick slush. The slushlike mixture was stirred and its temperature maintained at 80°C. At the end of 1.5 hrs., the liquid cleared as the slush disappeared. Heating was continued for an additional 3.5 hours and the resulting mixture was diluted with 100 ml. of benzene. The resulting slurry was filtered, the filtrate concentrated and the concentrate degassed. The resulting liquid analyzed 15% of the delta-4 isomer, 40% of the delta-3 isomer, 25% of the delta-1 isomer and 20% of phthalic anhydride. The consistency of this liquid product at the end of a few hours was that of a thick slush and it was still in that condition at the end of a 2 month storage period at room temperature.

Examples 14–21

In Examples 14–21 the isomerization was carried out by heating to the indicated temperature a mixture of 8 g. of delta-4 tetrahydrophthalic anhydride, 1 g. of the indicated acid anhydride and 0.15 g. of 10% palladium-on-carbon catalyst with occasional stirring. The results are tabularized below.

TABLE II

| Ex. No. | Added Anhydride | Reaction Time-Hrs. | Temp. °C. | Reaction Product Isomeric Mixture % | | | |
|---|---|---|---|---|---|---|---|
| | | | | delta-1 | delta-2 | delta-3 | delta-4 |
| 14 | succinic anhydride | 4 | 80° | 12 | 11 | 61 | 16 |
| 15 | dodecenyl succinic anhydride | 4 | 80° | 24 | 8 | 22 | 46 |
| 16 | endic anhydride | 4 | 80° | — | — | 11 | 89 |
| 17 | endic anhydride | 4 | 120° | 34 | — | 49 | 17 |
| 18 | delta-1 tetrahydrophthalic anhydride | 4 | 80° | 25 | 3 | 56 | 16 |
| 19 | itaconic anhydride | 4 | 80° | 10 | 6 | 53 | 31 |
| 20 | citraconic anhydride | 4 | 80° | 10 | — | 57 | 33 |
| 21 | 4-methyl tetrahydrophthalic anhydride | 4 | 80° | — | 11 | 39 | 50 |

It should be appreciated from the above examples that liquid mixtures of isomers of tetrahydrophthalic anhydride can be produced in accordance with this invention at relatively low temperatures and in a relatively short period of time. The time of reaction can be varied as desired by the user. In this connection it is noted that a mixture of isomers of tetrahydrophthalic anhydride which is in the solid state at room temperature, but which has a melting point below that of the delta-4 isomer is more convenient to use as an epoxy curing agent than the delta-4 isomer. Such a solid mixture can be produced in accordance with this invention in a shorter period of time than it takes to produce the liquid mixture of isomers. Although the time of reaction will vary depending on the other conditions of the process, a reaction time of about 15 minutes to 6 hrs. may be used to produce the solid or liquid mixtures. In general, a reaction time of about 1–4 hours will be most practical.

We claim:

1. An isomerization process for shifting the double bond of the delta-4 isomer of tetrahydrophthalic anhydride comprising isomerizing said delta-4 isomer above about room temperature but below about the melting point of the delta-4 isomer in the presence of a catalytic amount of palladium and, in a minor amount, at least about 0.1 wt.% of a liquid or solid second dicarboxylic acid anhydride, which has a molecular weight in excess of 100, which has a melting point below about 140°C, which is a curing agent for epoxy resins, and which is capable of forming a liquid mixture with said isomer at a temperature above room temperature but below the melting point of the delta-4 isomer, and initiating the isomerization above room temperature but below about the melting point of the delta-4 isomer.

2. A process according to claim 1 wherein the isomerization is initiated above about 60°C and the second anhydride is present in an amount up to about 20 wt.%.

3. An isomerization process according to claim 2 wherein the second acid anhydride is selected from the group consisting of hexahydrophthalic anhydride, phthalic anhydride and a mixture of two or more of the delta-1, delta-2 and delta-3 isomers of tetrahydrophthalic anhydride.

4. A process according to claim 3 wherein the temperature of the liquid mixture is raised above the melting point of said delta-4 isomer after a portion thereof has been isomerized.

5. A process for isomerizing the delta-4 isomer of tetrahydrophthalic anhydride comprising contacting said isomer at a temperature of about 60°C to about 120°C with about 0.001 wt.% to about 10 wt.% of palladium and about 0.1 wt.% to about 20 wt.% of a dicarboxylic acid anhydride which has a molecular weight above 100, which is a curing agent for epoxy resins, which is one other than said delta-4 isomer, which has a melting point below about 140°C, and which, in the liquid state, is miscible with said delta-4 isomer.

6. A process according to claim 5 including recovering an isomeric mixture of tetrahydrophthalic anhydride, which mixture is in the liquid state at about room temperature.

7. A process according to claim 5 wherein said acid anhydride is selected from the group consisting of hexahydrophthalic anhydride, phthalic anhydride and a mixture of two or more of the delta-1, delta-2 and delta-3 isomers of tetrahydrophthalic anhydride.

8. An isomerization process for shifting the double bond of either a delta-4 tetrahydrophthalic anhydride or an ester thereof comprising isomerizing the anhydride or ester in the presence of about 0.001 to about 10 wt.% of palladium and about 0.1 to about 20 wt.% of a dicarboxylic acid anhydride selected from the group consisting of hexahydrophthalic anhydride, phthalic anhydride and a mixture of two or more of the delta-1, delta-2 and delta-3 isomers of tetrahydrophthalic anhydride at a temperature of about 60°C to about 120°C.

9. A process according to claim 8 wherein delta-4 tetrahydrophthalic anhydride is isomerized and wherein the temperature is below the melting point of the delta-4 tetrahydrophthalic anhydride.

10. A process according to claim 8 wherein said temperature is above about 75°C.

11. A process according to claim 8 wherein the isomeric product of the isomerization is hydrogenated in part to convert a portion of the isomeric product to hexahydrophthalic anhydride.

* * * * *